(12) United States Patent
Di Fabio et al.

(10) Patent No.: US 7,273,871 B2
(45) Date of Patent: Sep. 25, 2007

(54) PHENYL-5,6,6A,7,8,9-HEXAHYDRO-4H-1,4, 9-TRIAZA-PHENALENE DERIVATIVES AS CRF ANTAGONISTS

(75) Inventors: Romano Di Fabio, Verona (IT); Collin F Regan, San Diego, CA (US); Yves St-Denis, Verona (IT); Fabrizio Micheli, Verona (IT); Michael K Schwaebe, San Diego, CA (US)

(73) Assignees: SB Pharmco Puerto Rico Inc., Hata Rey, PR (US); Neurocrine Biosciences Inc., San Diego, CA (US)

( * ) Notice: Subject to any disclaimer, the term of this patent is extended or adjusted under 35 U.S.C. 154(b) by 263 days.

(21) Appl. No.: 10/483,872

(22) PCT Filed: Jul. 15, 2002

(86) PCT No.: PCT/US02/22394

§ 371 (c)(1),
(2), (4) Date: Jul. 29, 2004

(87) PCT Pub. No.: WO03/008414

PCT Pub. Date: Jan. 30, 2003

(65) Prior Publication Data

US 2004/0242623 A1    Dec. 2, 2004

(30) Foreign Application Priority Data

Jul. 17, 2001 (GB) ................... 0117395.4

(51) Int. Cl.
*A61K 31/505* (2006.01)
*C07D 471/04* (2006.01)
*C07D 239/00* (2006.01)

(52) U.S. Cl. ................. 514/257; 514/267; 544/251

(58) Field of Classification Search ............... 514/257, 514/267; 544/251
See application file for complete search history.

(56) References Cited

U.S. PATENT DOCUMENTS

| 4,605,642 | A | 8/1986 | Rivier et al. |
| 6,440,960 | B1 * | 8/2002 | Haddach et al. ......... 514/224.5 |
| 6,531,475 | B1 * | 3/2003 | Haddach et al. ............ 514/250 |
| 6,583,143 | B2 * | 6/2003 | Haddach ................... 514/243 |
| 6,747,034 | B2 * | 6/2004 | Haddach et al. ............ 514/267 |

FOREIGN PATENT DOCUMENTS

| WO | WO 00/27846 | 5/2000 |
| WO | WO 00/27850 | 5/2000 |

* cited by examiner

*Primary Examiner*—Joseph K. McKane
*Assistant Examiner*—Susannah L. Chung
(74) *Attorney, Agent, or Firm*—Laura K. Madden; Loretta J. Sauermeich; Mary E. McCarthy

(57) ABSTRACT

The present invention relates to tricyclic pyridines compounds of formula (I) including stereoisomers, prodrugs and pharmaceutically acceptable salts or solvates thereof:

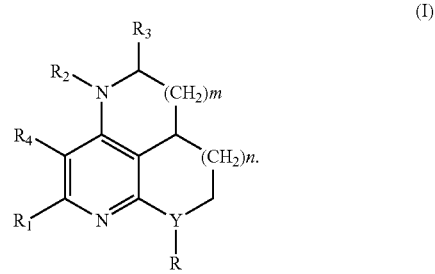

6 Claims, No Drawings

PHENYL-5,6,6A,7,8,9-HEXAHYDRO-4H-1,4,9-TRIAZA-PHENALENE DERIVATIVES AS CRF ANTAGONISTS

The present invention relates to tricyclic derivatives, to processes for their preparation, to pharmaceutical compositions containing them and to their use in therapy.

The first corticotropin-releasing factor (CRF) was isolated from ovine hypothalami and identified as a 41-amino acid peptide (Vale et al., Science 213: 1394-1397,1981). CRF has been found to produce profound alterations in endocrine, nervous and immune system function. CRF is believed to be the major physiological regulator of the basal and stress-release of adrenocorticotropic hormone ("ACTH"), Bendorphin, and other propiomelanocortin ("POMC")-derived peptides from the anterior pituitary (Vale et al., Science 213: 1394-1397,1981).

In addition to its role in stimulating the production of ACTH and POMC, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. Accordingly, clinical data suggests that CRF receptor antagonists may be useful in the treatment of the neuropsychiatric disorders manifesting hypersecretion of CRF, and, in particular, may represent novel antidepressant and/or anxiolytic drugs.

The first CRF receptor antagonists were peptides (see, e.g., Rivier et al., U.S. Pat. No. 4,605,642; Rivier et al., Science 224: 889,1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported.

WO 00/27846 discloses CRF receptor antagonists with the following general formula (A)

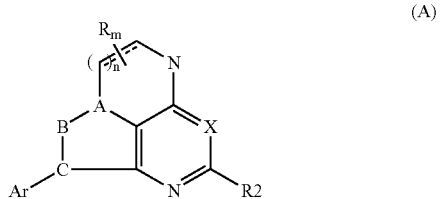

with the proviso that at least one of A, B and C is nitrogen, A, B and C are not all nitrogen and either A-B or B-C is a double bond. A, B, C and X may be nitrogen or carbon.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

In particular the invention relates to novel compounds which are potent and specific antagonists of corticotropin-releasing factor (CRF) receptors.

The present invention provides compounds of formula (I) including stereoisomers, prodrugs and pharmaceutically acceptable salts and solvates thereof

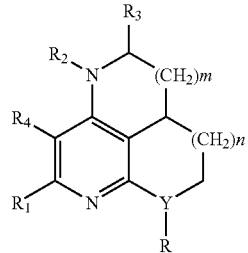

wherein

R is aryl or heteroaryl, wherein each of the above groups R may be substituted by 1 to 4 substituents indendently selected from the group consisting of:
halogen, C1-C6 alkyl, C1-C6 alkoxy, halo C1-C6 alkyl, C2-C6 alkenyl, C2-C6 alkynyl, halo C1-C6 alkoxy, C1-C6 mono or dialkylamino, nitro, cyano and a group $R_5$;

$R_1$ is hydrogen, C1-C6 alkyl, C2-C6 alkenyl, C2-C6 alkynyl, halo C1-C6 alkyl, halo C1-C6 alkoxy, $NH_2$, halogen or cyano;

$R_2$ is hydrogen or $C(H)_n(R_6)_q(CH_2)_pZR_7$;

$R_3$ is hydrogen, C2-C6 alkenyl, C2-C6 alkynyl or $[CH(R_6)(CH_2)_p]_mZR_7$;

$R_4$ hydrogen, C1-C6 alkyl, halogen or halo C1-C6 alkyl;

$R_5$ is C3-C7 cycloalkyl, which may contain one or more double bonds;
aryl; or a 5-6 membered heterocycle;
wherein each of the above groups $R_5$ may be substituted by one or more groups selected from: halogen, C1-C6 alkyl, C1-C6 alkoxy, halo C1-C6 alkyl, C2-C6 alkenyl, C2-C6 alkynyl, halo C1-C6 alkoxy, C1-C6 mono or dialkylamino, nitro, and cyano;

$R_6$ is hydrogen, C2-C6 alkenyl, C2-C6 alkynyl or $(CH_2)_pZR_7$;

$R_7$ is C1-C6 alkyl, which may be substituted by one or more groups selected from halogen, halo C1-C6 alkyl, C2-C6 alkenyl, C2-C6 alkynyl, halo C1-C6 alkoxy, C1-C6 alkoxy, C1-C6 mono or dialkylamino, nitro, cyano and a group $R_5$;

Y is carbon or nitrogen;
m and n are independently 0 or 1;
p is 0 or an integer from 1 to 4;
q is 1 or 2;
z is a bond, O, NH or S.

Acid addition salts of the free base amino compounds of the present invention may be prepared by methods well known in the art, and may be formed from organic and inorganic acids. Suitable organic acids include maleic, malic, fumaric, benzoic, ascorbic, succinic, methanesulfonic, p-toluensulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

The solvates may, for example, be hydrates.

References hereinafter to a compound according to the invention include both compounds of formula (I) and their pharmaceutically acceptable acid addition salts together with pharmaceutically acceptable solvates.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as recemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention.

The term C1-C6 alkyl as used herein as a group or a part of the group refers to a straight or branched alkyl group containing from 1 to 6 carbon atoms; examples of such groups include methyl, ethyl, propyl, isopropyl, n-butyl, isobutyl, tert butyl, pentyl or hexyl.

The term C3-C7 cycloalkyl group means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term halogen refers to a fluorine, chlorine, bromine or iodine atom.

The term halo C1-C6 alkyl means an alkyl group having one to six carbon atoms and wherein at least one hydrogen atom is replaced with halogen such as for example a trifluoromethyl group and the like.

The term C2-C6 alkenyl defines straight or branched chain hydrocarbon radicals containing one or more double bond and having from 2 to 6 carbon atoms such as, for example, ethenyl, 2-propenyl, 3-butenyl, 2-butenyl, 2-pentenyl, 3-pentenyl, 3-methyl-2-butenyl or 3-hexenyl and the like.

The term C1-C6 alkoxy group may be a straight or a branched chain alkoxy group containing from 1 to 6 carbon atoms, for example methoxy, ethoxy, propoxy, prop-2-oxy, butoxy, but-2-oxy or methylprop-2-oxy and the like.

The term halo C1-C6 alkoxy group may be a C1-C6 alkoxy group as defined before substituted with at least one halogen, preferably fluorine, such as $OCHF_2$, or $OCF_3$.

The term C2-C6 alkynyl defines straight or branched chain hydrocarbon radicals containing one or more triple bond and having from 2 to 6 carbon atoms including acetylenyl, propynyl, 1-butynyl, 1-pentynyl, 3-methyl-1-butynyl and the like.

The term C1-C6 mono or dialkylamino represents an amino group independently substituted with one or two C1-C6 alkyl groups, as defined before.

The term aryl means an aromatic carbocyclic moiety such as phenyl, biphenyl or naphthyl.

The term heteroaryl means an aromatic heterocycle ring of 5- to 10 members and having at least one heteroatom selected from nitrogen, oxygen and sulfur, and containing at least 1 carbon atom, including both mono- and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term 5-6 membered heterocycle means, according to the above definition, a monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. The heterocycle may be attached via any heteroatom or carbon atom. Thus, the term includes (but is not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

Representative compounds of this invention include the following structure (Ia) and (Ib)

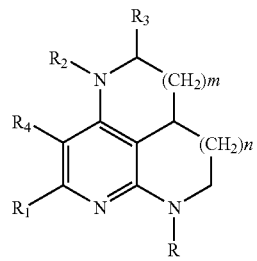

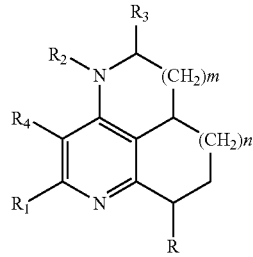

wherein, respectively, Y corresponds to a carbon and a nitrogen atom.

Representative compounds of this invention also include the following structures (II), and (IIa), wherein, respectively, m is 1 and 0.

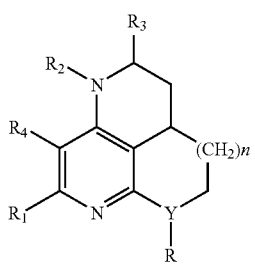
(II)

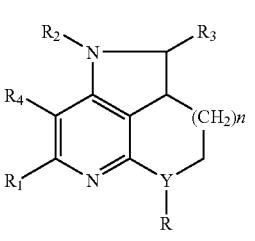
(IIa)

Depending upon the choice of m and n in the compounds of formula (I), the representative compounds of this invention include the following compounds (IIIa), (IIIb) and (IIIc).

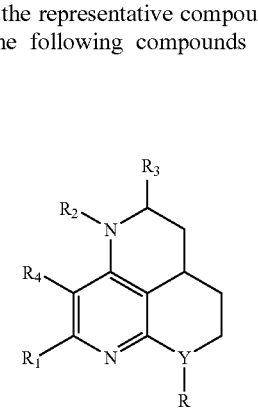
(IIIa)

(IIIb)

(IIIc)

Depending upon the choice of Y, m, n the representative compounds of this invention include, but are not limited to, the following compounds (IVa), (IVb) and (IVc).

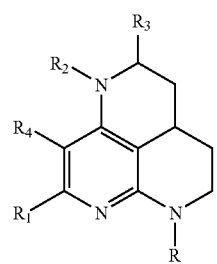
(IVa)

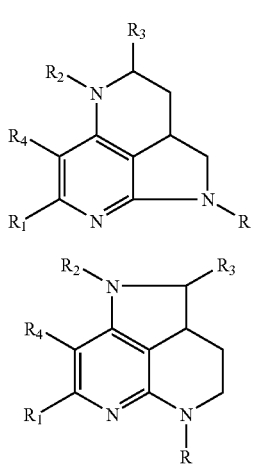
(IVb)

(IVc)

More specific embodiments of the invention include, but are not limited to, compounds of the formula (I); (II), (IIa), (IIIa), (IIIb), (IIIc), (IVa), (IVb), (IVc):

wherein:
$R_2$ and $R_3$ are not simultaneously hydrogen;
$R_4$ is hydrogen.

Further specific embodiments of the invention include, but are not limited to, compounds of the formula (I); (II), (IIa), (IIIa), (IIIb), (IIIc), (IVa), (IVb), (IVc):

wherein:
$R_1$ is C1-C3 alkyl group or halo C1-C3 alkyl group, preferably methyl or trifluoromethyl.

Preferred embodiments of the invention include, but are not limited to, compounds of the formula (I); (II), (IIa), (IIIa), (IIIb), (IIIc), (IVa), (IVb), (IVc):

wherein:
$R_2$ and $R_3$ are not simultaneously hydrogen;
$R_4$ is hydrogen; and
$R_1$ is C1-C3 alkyl group or halo C1-C3 alkyl group, preferably methyl or trifluoromethyl;

More preferred embodiments of the invention include, but are not limited to, compounds of the formula (I); (II), (IIa), (IIa), (IIb), (IIIc), (IVa), (IVb), (IVc):

wherein:
$R_2$ and $R_3$ are not simultaneously hydrogen;
$R_4$ is hydrogen;
$R_1$ is C1-C3 alkyl group or halo C1-C3 alkyl group, preferably methyl or trifluoromethyl;
R is an aryl group selected from: 2,4-dichlorophenyl, 2-chloro-4-methylphenyl, 2-chloro-4-trifluoromethyl, 2-chloro-4-methoxyphenyl, 2,4,5-trimethylphenyl, 2,4-dimethyl-phenyl, 2-methyl-4-methoxyphenyl, 2-methyl-4-chlorophenyl, 2-methyl-4-trifluoromethyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl, 2-methoxy-4-methylphenyl, 2-trifluoromethyl-4-chlorophenyl, 2,4-trifluoromethylphenyl, 2-trifluoromethyl-4-methylphenyl, 2-trifluoromethyl-4-methoxyphenyl, 2-bromo-4-isopropylphenyl, 2-methyl-4-cyanophenyl, 2-chloro-4-cyanophenyl, 4-methyl-6-dimethylaminopyridin-3-yl, 4-dimethylamino-6-methylpyridin-3-yl, 6-dimethylamino-pyridin-3-yl and 4-dimethylamino-pyridin-3-yl.

Preferred compounds according to the invention are:
1-(4-methoxy-2-methylphenyl)-7-methyl-5-(1-propyl-butyl)-1,2,2a,3,4,5-hexahydro-1,5,8-triaza-acenaphtylene;
1-(2,4-dimethylphenyl)-7-methyl-5-(1-propyl-butyl)-1,2,2a,3,4,5-hexahydro-1,5,8-triaza-acenaphtylene;
1-(2-chloro-4-methylphenyl)-7-methyl-5-(1-propyl-butyl)-1,2,2a,3,4,5-hexahydro-1,5,8-triaza-acenaphtylene;
9-(2,4-dimethyl-phenyl)-2-methyl-4-(1-propyl-butyl)-5,6,6a,7,8,9-hexahydro-4H-1,4,9-triaza-phenalene;
9-(4-methoxy-2-methyl-phenyl)-2-methyl-4-(1-propyl-butyl)-5,6,6a,7,8,9-hexahydro-4H-1,4,9-triaza-phenalene.

Compounds of formula (I), and salts and solvates thereof, may be prepared by the general methods outlined hereinafter. In the following description, the groups R, $R_1$, $R_2$, $R_3$, $R_4$, $R_5$, $R_6$, $R_7$, X, Y, Z, m, n, p and q have the meaning as previously defined for compounds of formula (I) unless otherwise stated.

Compounds of formula (II), in which $R_4$ is hydrogen, may be conveniently prepared according to the following Scheme 1:

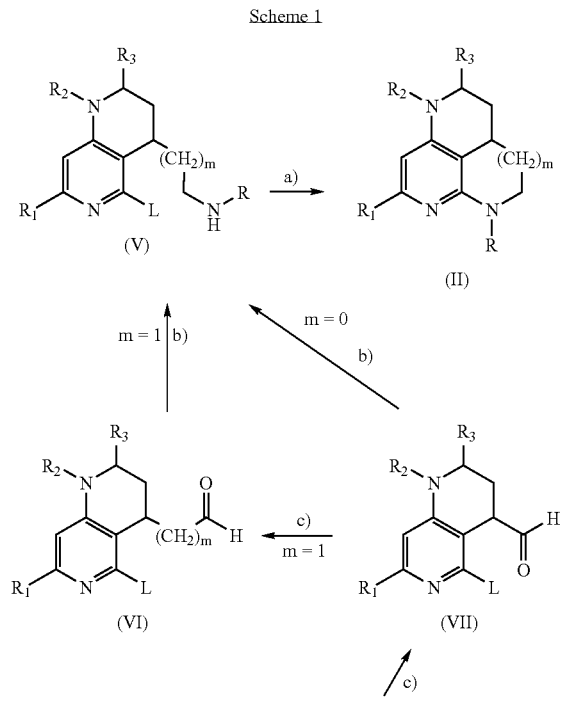

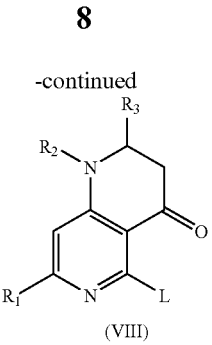

in which:
step a stands for intramolecular cyclisation by heating in a high boiling suitable solvent (like diphenyl ether) at a temperature more than 150° C. and eventually in the presence of an acid catalyst;
step b stands for reductive amination with the amine $RNH_2$ using a suitable reducing agent, like for example $NaBH(OAc)_3$;
step c stands for formation of the aldehyde group by Wittig reaction with (methoxymethyl)diphenyl phosphine oxide in the usual conditions, followed by acid hydrolysis of the obtained enol ether.

Compound of formula (VIII) may be prepared according to the following Scheme 2:

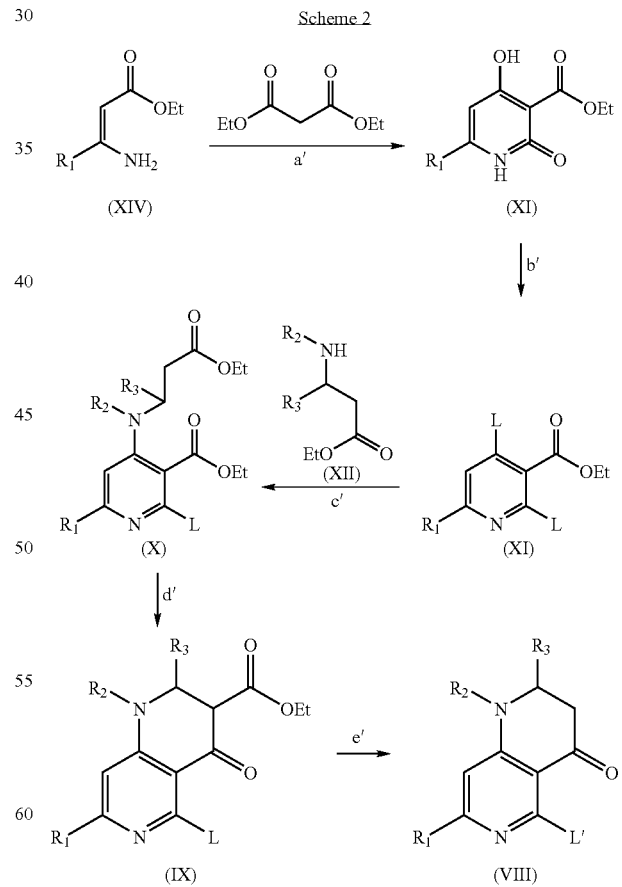

in which:
step a' stands for intramolecular cyclisation by Claisen reaction;

step b' stands for conversion of the hydroxy groups in a suitable leaving group L, selected from a group consisting of: halogen or a reactive residue of a sulphonic acid (mesylate, triflate), preferably triflate (OTf);
step c' stands for reaction with the suitable amine (XII) in basic conditions (e.g. $K_2CO_3$) and in an aprotic dipolar solvent;
step d' stands for intramolecular cyclisation in basic conditions (e.g. t-BuOK);

step e' stands for decarboxylation in acid conditions followed by conversion of L group in a different leaving group, preferably chloride.

Compounds of formula (IVc), in which $R_4$ is hydrogen, may be conveniently prepared according to the following Scheme 3, starting from compounds of formula (XV), whose preparation is known from the literature (see the Experimental Part for the details):

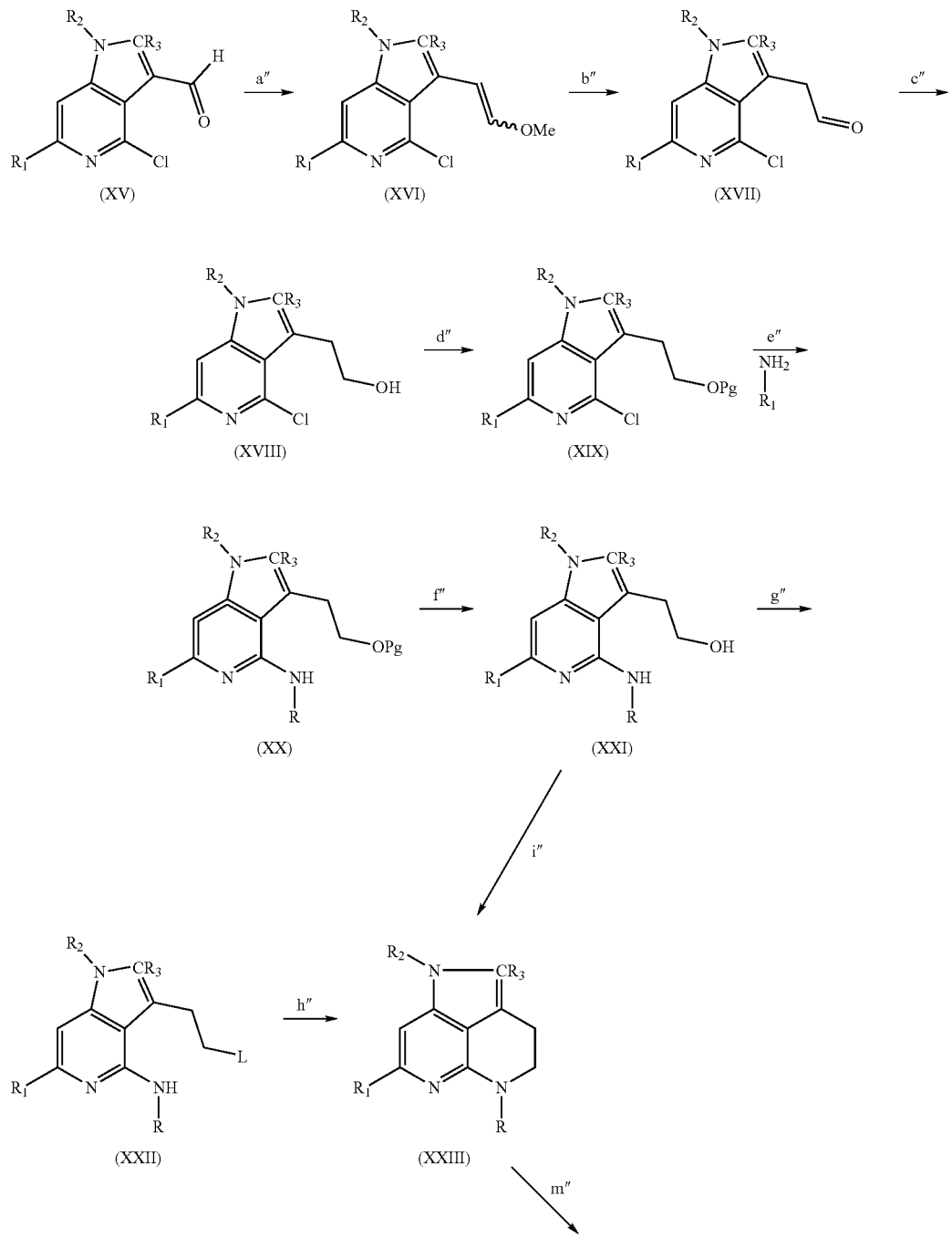

-continued

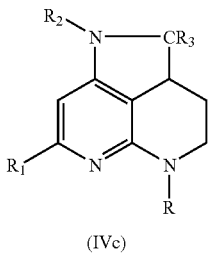

(IVc)

in which:
step a" stands for homologation of a carbon atom by Wittig reaction with the suitable ylide, in the presence of a suitable organic base like n-BuLi. The reaction is carried out in an aprotic solvent such as acetonitrile or an ether such as tetrahydrofuran;
step b" stands for usual hydrolysis in acid conditions (e.g. HCl in THF) of the enol ether (XVI);
step c" stands for reduction of the aldehyde group of compounds (XVII) by a suitable reducing agent (e.g. $NaBH_4$);
step d" stands for protection of the hydroxy group of compounds (XVIII), preferably with t-BuMe$_2$SiCl (TBS), in DMF with imidazole and DMAP as catalyst (0° C. to r.t);
step e" stands for microwave assisted Buchwald reaction with the suitable aniline derivative $RNH_2$;
step f" stands for deprotection of the hydroxy protecting group (e.g. Et$_3$N-3HF in DMF at r.t. overnight);
step g" stands for conversion of the hydroxy group in a leaving group, such as mesylate;
step h" stands for intramolecular cyclisation in basic conditions; alternatively, the compounds (XXIII) may be obtained from compounds (XXI) according to step i;
step i" stands for intramolecular cyclisation, for example by mesylation of the hydroxy group in basic conditions (i.e. Et$_3$N) followed by in situ cyclisation;
step m" stands for reduction of the enamine derivative (XXIII) with a suitable reducing agent, such as Mg in MeOH or $NaBH_4$.

Compounds of formula (II), (IVc), (VIII) may be prepared analogously following previous Schemes 1 to 3, starting from substrate containing already the group $R_4$.

Examples of suitable hydroxy protecting group include trihydrocarbyl silyl ethers such as the trimethylsilyl or t-butyldimethylsilyl ether. The hydroxyl protecting groups may be removed by well-known standard procedures (such as those described in Protective Groups in Organic Chemistry, pages 46-119, Edited by J F W McOmie (Plenum Press, 1973)). For example when Pg is a t-butyldimethylsilyl group, this may be removed by treatment with triethylamine trihydrofluoride.

Pharmaceutical acceptable salts may also be prepared from other salts, including other pharmaceutically acceptable salts, of the compound of formula (I) using conventional methods.

The compounds of formula (I) may readily be isolated in association with solvent molecules by crystallisation or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I. Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

The CRF receptor antagonists of the present invention demonstrate activity at the CRF receptor site including CRF 1 and CRF 2 receptors and may be used in the treatment of conditions mediated by CRF or CRF receptors.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7: 88,1987) and Battaglia et al. (Synapse 1: 572,1987).

The CRF receptors-binding assay was performed by using the homogeneous technique of scintillation proximity (SPA). The ligand binds to recombinant membrane preparation expressing the CRF receptors which in turn bind to wheat germ agglutinin coated SPA beads. In the Experimental Part will be disclosed the details of the experiments.

With reference to CRF receptor binding affinities, CRF receptor antagonists of this invention have a Ki less than 10 μm. In a preferred embodiment of this invention, a CRF receptor antagonist has a Ki of less than 10 μm.

As set forth in greater detail below, the Ki values of representative compounds of this invention were assayed by the methods set forth in Example 4.

Compounds of the invention are useful in the treatment of central nervous system disorders where CRF receptors are involved. In particular in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganised schizophrenia, catatonic schizophrenia, undifferentiated schizophrenia, residual schizoprenia.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neui opathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa and bulimia.

Compounds of the invention are also useful in the treatment of sleep disorders including dysomnia, insomnia, sleep apnea, narcolepsy, and circadian ritmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative hypnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome (IBS); skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by CRF.

In an alternative or further aspect there is provided a method for the treatment of a mammal, including man, in particular in the treatment of condition mediated by CRF, comprising administration of an effective amount of a compound of formula (I) or a pharmaceutically acceptable salt or a solvate thereof.

It will be appreciated that reference to treatment is intended to include prophylaxis as well as the alleviation of established symptoms.

Compounds of formula (I) may be administered as the raw chemical but the active ingredient is preferably presented as a pharmaceutical formulation.

Accordingly, the invention also provides a pharmaceutical composition, which comprises at least one compound of formula (I) or a pharmaceutically acceptable salt thereof and formulated, for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus for parenteral administration a daily dose will typically be in the range of 1 to about 100 mg, preferably 1 to 80 mg per day. For oral administration a daily dose will typically be within the range 1 to 300 mg e.g. 1 to 100 mg.

EXAMPLES

In the Intermediates and Examples unless otherwise stated:

Melting points (m.p.) were determined on a Gallenkamp m.p. apparatus and are uncorrected.

All temperatures refers to ° C. Infrared spectra were measured on a FT-IR instrument. Proton Magnetic Resonance ($^1$H-NMR) spectra were recorded at 400 MHz or 300 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Column chromatography was carried out over silica gel (Merck AG Darmstaadt, Germany). The following abbreviations are used in text: EtOAc=ethyl acetate, cHex=cyclohexane, CH$_2$Cl$_2$=dichloromethane, Et$_2$O=dietyl ether, DMF=N,N-dimethylformamide, DIPEA=N,N-diisopropylethylamine, MeOH=methanol, Et$_3$N=triethylamine, TFA=trifluoroacetic acid, THF=tetrahydrofuran, DIBAL- H=diisobutylaluminium hydride, DMAP=dimethylaminopyridine, LHMDS=lithium hexamethyldisilazane, MTBE=methyl-tert-butyl ether; Tlc refers to thin layer chromatography on silica plates, and dried refers to a solution dried over anhydrous sodium sulphate; r.t. (RT) refers to room temperature.

Intermediate 1

4-Hydroxy-6-methyl-2-oxo-1,2-dihydro-pyridine-3-carboxylic acid ethyl ester

In a 22 L vessel fitted with a mechanical stirrer and distillation head was charged 2.5 L (16.47 mol) diethyl malonate followed by 4.0 L diphenyl ether. Agitation was started and 1.12 Kg (16.47 mol, 1 eq) of sodium ethoxide was added via a powder funnel. The mixture was gradually, heated to 160° C. and the liberated ethanol was removed via distillation, approximately 950 mL. After 30 min, ethanol distillation ceased and 2.127 Kg (16.47 mol, 1 eq) of 3-amino-but-2-enoic acid ethyl ester was added, and the resulting ethanol formed removed via distillation. After 30 minutes the mechanical stirrer could no longer stir the foamy mass. At this point, external heating was ceased and the mixture allowed to cool to ambient temperature. To the mixture was charged 4 L of methyl-tert-butyl ether (MTBE) and the granular solid broken up with a spatula. The solid was filtered and washed with MTBE. To the solid was then added 100 mL of conc. HCl and 2 L of chloroform to solublize the mixture. The mixture was then taken up three times in 4 L chloroform, and decanted into a 20 L bucket. The combined organic phases were dried over sodium sulfate. The mixture was concentrated in vacuo to afford an orange gummy mass, which was triturated with MTBE and filtered, washing the filter cake with MTBE. The resulting solid was recrystallized from ethanol to afford the desired product as pinkish needles.

Subsequent mother liquors were concentrated and chilled to afford further crops of pure final product, giving a total of 1.477 kg, in a 46% yield.

$^1$H NMR (CDCl$_3$) δ: 5.84 (s, 1H), 4.43 (q, 2H), 2.31 (s, 3H), 1.43 (t, 3H).

Intermediate 2

6-Methyl-2,4-bis-trifluoromethanesulfonyloxy-nicotinic acid ethyl ester

In a 5 L round bottom 3-neck flask equipped with a mechanical stirrer and nitrogen bubbler was charged 1 L of anhydrous dichloromethane. To the solution was charged 320 g (1.62 mol) of intermediate 1 and 490 mL (3.5 mol, 2.2 eq.) of triethylamine. The mixture was cooled to <5° C. with an ice-bath and 950 g (3.37 mol, 2.08 eq.) of triflic arhydride in 500 mL of dichloromethane was added via a 2 L addition funnel over 2 hours. The mixture was allowed to warm to ambient temperature and stir for an additional 2 hours. The reaction was quenched with 500 mL of water and the organic phase separated. The organic phase was washed twice with 200 mL of 1 N HCl, 100 mL of brine, dried over magnesium sulfate and filtered over a pad of silica gel (80×120 mm) eluting with ethyl ether.

The solvent was removed in vacuo to afford 790 g of the desired product as an oil in quantitative yield.

GCMS T$_r$=4.97 min MS (70 eV, EI) m/z 461 (2), 433 (35), 416 (40), 284 (75)

Intermediate 3

3-(1-Propyl-butylamino)-propionic acid ethyl ester

To a 12 L 3-neck flask equipped with a mechanical stirrer and nitrogen inlet was charged 400 g (2.6 mol) of β-alanine, 2250 L of dichloromethane and 2.3 L of ethanol. Agitation was begun and 1.09 L (7.8 mol, 3 eq) of triethyl amine and 364 mL (2.6 mol, 1 eq) of 4-heptanone were added. The mixture was cooled to <10° C. and 1.65 Kg (7.8 mol, 3 eq) of sodium triacetoxy borohydride. Mixture kept <15° C. and stirred for 24 hrs.

Note: reaction becomes exothermic above 25° C., proper cooling must be maintained. The reaction was check for completion by GC. The reaction was quenched with 1 L of 5 M sodium hydroxide keeping the reaction temp <10° C. The mixture was diluted with brine and the organic phase separated. The organic phase was dried over sodium sulfate and the solvent removed in vacuo. The crude residue was diluted with ethyl ether and filtered. The filtrate was concentrated in vacuo affording 333 g of a yellow oil in a 59% yield.

Intermediate 4

4[(2-Ethoxycarbonyl-ethyl)-(1-propyl-butyl)-amino]-6-methyl-2-trifluoromethansulfonyloxy-nicotinic acid ethyl ester In a 5 L 3-neck flask equipped with a mechanical stirrer, thermometer, nitrogen bubbler and addition funnel was charged 105 g (228 mmol) of intermediate 2. To the reactor were charged 300 mL of anhydrous acetonitrile and 48 mL (343 mmol, 1.5 eq.) of triethylamine and the mixture cooled to <5° C. with an ice bath. To the mixture was charged using the addition funnel 49.1 g (244 mmol, 1.08 eq.) of intermediate 3 diluted with 300 mL of acetonitrile. The addition was completed over 2 hr keeping the reaction temperature <10° C. The mixture was allowed to warm to ambient temperature and stir for an additional 2 hours. The reaction was checked for completion by GC. The reaction mixture was diluted with 500 mL of dichloromethane and washed twice with 100 mL of 1 N HCl, 100 mL of brine, dried over magnesium sulfate and filtered over a pad of silica gel (50×80 mm) eluting with ethyl ether. The solvent was removed in vacuo and the resulting material was chromatographed on silica gel eluting with ethyl acetate/hexanes 1:3 (R$_f$=0.25). The solvent was removed in vacuo to afford 75 g of the deseired product as a colorless oil in a 77% yield.

GCMS Tr=7.56 min MS (70 eV, EI) m/z 497 [M-29] (2), 483 (100), 439 (5)

Intermediate 5

7-Methyl 4-oxo-1-(1-propyl-butyl)-5-trifluoromethansulfonyloxy-1,2,3,4-tetrahydro-[1,6]-naphtyridine-3-carboxylic acid ethyl ester In a 2 L 3-neck flask equipped with a mechanical stirrer and nitrogen bubbler was charged 75 g (177 mmol) of intermediate 4 and 500 mL of anhydrous ethyl ether. Agitation was begun and 20.8 g (186 mmol, 1.05 eq.) of potassium tert-butoxide was added via a powder funnel. The mixture was allowed to stir at ambient temperature for 1 hr. The reaction was checked by TLC to monitor disappearance of starting material. The mixture was filtered over celite and the solvent was removed in vacuo to afford 56 g of the potassium salt of the desired product as a brignt yellow solid in a 61% yield.

MS (M+1) 481.

Intermediate 6

5-Chloro-7-methyl-1-(1-propyl-butyl)-2,3-dihydro-1H-[1,6]naphtyridin-4-one

In a 1 L 3-neck flask equipped with a mechanical stirrer, condenser and nitrogen bubbler was charged 56 g (108 mmol) of intermediate 5 followed by 100 mL of 4M HCl in dioxane. The mixture was allowed to stir for 2 hours at ambient temperature. Then 100 mL of 4 N HCl was added and the mixture was heated to reflux for 12 hours. The mixture was cooled to ambient temperature and carefully neutralized with approximately 200 mL of 4N NaOH. The organic phase was separated and the aqueous layer was extracted 4 times with 100 mL of ethyl acetate. The combined organic phases were dried over magnesium sulfate and filtered over a pad of silica gel (50×80 mm) eluting with ethyl ether. The solvent was removed in vacuo to afford 24 g of the desired product as an oil that solidified over 2 days in a 75% yield.

GCMS Tr=8.15 min. MS (70 eV, EI) m/z 294 (7), 251 (100), 223 (17).

Intermediate 7

5-Chloro-4-methoxymetilene-7-methyl-1-(1-propyl-butyl)-1,2,3,4-tetrahydro-[1,6]-naphtyridine To a cooled suspension (−60° C.) of (methoxymethylene) diphenylphosphine oxide (12.7 g, 1.5 eq) in 70 mL anhydrous THF was added 24 mL of LDA (2.0M in THF/heptane, 1.4 eq) dropwise not allowing reaction temperature to rise above −50° C. After addition of LDA, the rxn was warmed to 0° C. The reaction was cooled to −60° C. and intermediate 6 (10.077 g, 1.0 eq) was dissolved in 50 mL anhydrous THF and added dropwise not allowing reaction temperature to rise above −45° C. Once added, the reaction was warmed to 0° C. and NaH (60% dispersion in mineral oil) was added (2.74 g, 2.0 eq). The reaction was stirred for 5 min at 0° C., then warmed to room temp. The reaction was quenched after 30 minutes with the dropwise addition of water (20 mL). The THF was removed in vacuo and the residue was extracted with ethyl acetate (3×50 mL). The combined organics were washed with brine, dried over sodium sulfate, filtered, and concentrated in vacuo. The resulting material was chromatographed on silica gel, the phosphite derivative (3.231 g, 17.5%) eluting with ethyl acetate, while the starting material (3.033 g, 30.1%) and the desired product (3.542 g, 32.1%) eluted with 30% ethyl acetate/hexanes. The hydrolysis of the phosphite derivative in the usual conditions (NaH/THF, 60° C.) has permitted to recover intermediate 7 as a pale yellow solid (1.73 g, 90%).

GC/MS T=7.84 min., MS (70 eV, EI) m/z 322 [M] (20), 279 (100). $^1$H NMR (CDCl$_3$) δ: 6.9 (s, 1H), 6.35 (s, 1H), 3.86 (m, 1H), 3.72 (s, 3H), 3.15 (t, 2H), 2.46 (t, 2H), 2.34 (s, 3H), 1.5 (m, 4H), 1.25 (m, 4H), 0.87 (t, 6H).

Intermediate 8

5-Chloro-7-methyl-1-(1-propyl-butyl)-1,2,3,4-tetrahydro-[1,6]naphtyridine-4-carbaldehyde 0.4 g of intermediate 7 was added to 10 mL of 6M HCl and stirred for 30 min. The reaction was then basified with a saturated aqueous bicarbonate solution. This was extracted with ethyl acetate (3×50 mL). The combined organics were washed with brine, dried over sodium sulfate, and filtered over a pad of silica gel eluting with 30% ethyl acetate/hexanes.

Concentration in vacuo yielded an oil (0.35 g, 91%).

MS (M+1) 309. $^1$H NMR (CDCl$_3$) δ: 9.78 (s, 1H), 6.43 (s, 1H), 3.88 (m, 1H), 3.19 (dm, 2H), 2.8 (dt, 1H), 2.45 (dq, 2H), 2.38 (s, 3H), 1.5 (m, 4H), 1.2 (m, 4H), 0.85 (dt, 6H).

Intermediate 9

5-Chloro-4-(2-methoxy-vinyl)-7-methyl-1-(1-propyl-butyl)-1,2,3,4-tetrahydro-[1,6]-naphtyridine The exact same methodology used to make intermediate 7 was used to make the desired product starting from intermediate 8.

MS (M+1) 337. R$_f$=0.6 in 30% ethyl acetate/hexanes.

Intermediate 10

[5-Chloro-7-methyl-1-(1-propyl-butyl)-1,2,3,4-tetrahydro-[1,6]naphtyridin-4-yl]-acetaldehyde 0.22 g of intermediate 9 was dissolved in 6M HCl (3 mL) and stirred at room temp for 30 min. The reaction was then basified with a saturated aqueous bicarbonate solution. This was extracted with ethyl acetate (3×25 mL). The combined organics were washed with brine, dried over sodium sulfate, and filtered over a pad of silica gel eluting with 30% ethyl acetate/hexanes. Concentration in vacuo yielded an oil (0.182 g, 87%).

MS (M+1) 323. R$_f$=0.5 in 30% ethyl acetate/hexanes.

Intermediate 11

4-Chloro-3-(2-methoxy-vinyl)-6-methyl-1-(1-propyl-butyl)-1H-pyrrolo[3,2-c]pyridine To a solution of (methoxymethyl)-triphenylphosphonium chloride (70 mg, 3 eq) in anh. THF (1 mL), at 0° C., under N$_2$, BuLi 1.6M in THF (128 μL, 3 eq) was added dropwise. The resulting red reaction mixture was stirred at 0° C. for 10 min and further 20 min at r.t. Then the reaction mixture was cooled at 0° C. and a solution of 4-chloro-6-methyl-1-(1-propyl-butyl)-1H-pyrrolo[3,2-c]pyridine-3-carbaldehyde (prepared following procedures reported in J. Heterocyclic Chem.; 1996, 33, 303; J. Heterocyclic Chem.; 1992, 29, 359; Heterocycles; 2000, 53, 11, 2415; Tetrahedron; 1985, 41, 10, 1945. analytical data: NMR ($^1$H, DMSO): δ 8.49 (s, 1H), 7.70 (s, 1H), 10.4 (s, 1H), 2.53 (s, 3H), 4.57 (m, 1H), 1.92/1.79 (m/m, 4H), 1.70/0.90 (m/m, 4H), 0.77 (t, 6H); MS (m/z): 293 [MH]$^+$) (20 mg, 0.068 mmol) in anh. THF (1 mL) was added dropwise.

The reaction mixture was stirred at r.t. for 1 hr. Then water (3 mL) was added and the product was extracted with EtOAc (3×5 mL). The combined organic layers were washed with sat.aq. NaCl (1×5 mL) and dried over anh. Na$_2$SO$_4$. The solids were filtered and the solvent evaporated to give a crude product, which was purified by flash chromatography (silica gel, cHex/EtOAc 95:05). The desired product was obtained as a yellow oil (15 mg, 0.046 mmol, 70%)

NMR ($^1$H, CDCl$_3$): δ (trans) 6.98 (s, 1H), 2.59 (s, 3H), 6.69, (s, 1H), 6.81 (d, 1H), 6.40 (d, 1H), 4.21 (m, 1H), 1.82 (m, 4H), 1.53 (m, 4H), 0.85 (dt, 6H), 3.83 (s, 3H0; (cis) 6.94 (s, 1H), 2.59 (s, 3H), 7.62, (s, 1H), 4.21 (m, 1H), 1.82 (m, 4H), 1.53 (m, 4H), 0.85 (dt, 6H), 6.19 (d, 1H), 6.30 (d, 1H), 3.72 (s, 3H), MS (m/z): 321 [MH]$^+$.

Intermediate 12

[4-Chloro-6-methyl-1-(1-propyl-butyl)-1H-pyrrolo[3,2-c]pyridin-3-yl]-acetaldehyde To a solution of intermediate 11 (85 mg, 0.26 mmol) in anh. THF (2 mL) at 0° C., under $N_2$, HCl 2N (2 mL) was added dropwise. The resulting yellow reaction mixture was stirred at 70° C. for 1.5 hr. Then sat.aq. $NaHCO_3$ (1 mL) was added and the product was extracted with EtOAc (3×5 mL). The combined organic layers were washed with sat.aq. NaCl (1×5 mL) and dried over anh. $Na_2SO_4$. The solids were filtered and the solvent evaporated to give a crude product, which was purified by flash chromatography (silica gel, cHex/EtOAc 8:2). The desired product was obtained as a yellow oil (55 mg, 0.179 mmol, 70%)

NMR ($^1$H, CDCl$_3$): δ 9.85 (s, 1H), 7.07 (s, 1H), 7.01, (s, 1H), 4.21 (m, 1H), 4.04 (s, 2H), 2.60 (s, 3H), 1.82 (m, 4H), 1.16 (m, 4H), 0.85 (dt, 6H). MS (m/z): 307 [MH]$^+$.

Intermediate 13

[4-Chloro-6-methyl-1-(1-propyl-butyl)-1H-pyrrolo[3,2-c]pyridin-3-yl]-ethanol To a solution of intermediate 12 (53 mg, 0.173 mmol) in anh. MeOH (4 mL) at 0° C., under $N_2$, $NaBH_4$ (13.1 mg, 2 eq) was added. The reaction mixture was stirred at 0° C. for 1 hr. Then water (1 mL) was added and the product was extracted with EtOAc (3×5 mL). The combined organic layers were washed with sat.aq. NaCl (1×5 mL) and dried over anh. $Na_2SO_4$. The solids were filtered and the solvent evaporated to give a crude product, which was purified by flash chromatography (silica gel, cHex/EtOAc 7:3). The desired product was obtained as a yellow oil (49.8 mg, 0.161 mmol, 93%)

NMR ($^1$H, DMSO): δ 7.37 (s, 1H), 7.33, (s, 1H), 4.63 (t, 1H), 3.64 (t, 2H), 3.01 (t, 2H), 2.44 (s, 3H), 1.77 (m, 4H), 0.89-1.79 (m, 4H), 0.77 (t, 6H).

MS (m/z): 309 [MH]$^+$.

Intermediate 14

3-[2-(tert-Butyl-dimethyl-silanyloxy)-ethyl]-4-chloro-6-methyl-1-(1-propyl-butyl)-1H-pyrrolo[3,2-c]pyridine To a solution of intermediate 13 (49.8 mg, 0.173 mmol) in anh. DMF (2 mL) at 0° C., under $N_2$, imidazole (110 mg, 10 eq), TBSCl (67 mg, 2.8 eq), DMAP (2 mg, 0.1 eq) were added. The reaction mixture was stirred at r.t. overnight. Then water (1 mL) was added and the product was extracted with Et$_2$O (3×5 mL). The combined organic layers were washed with sat.aq. NaCl (1×5 mL) and dried over anh. $Na_2SO_4$. The solids were filtered and the solvent evaporated to give a crude product, which was purified by flash chromatography (silica gel, cHex/EtOAc 9:1). The desired product was obtained as a yellow oil (65 mg, 0.154 mmol, 95%).

NMR ($^1$H, DMSO): δ 6.95 (s/s, 1/1H), 4.17 (m, 1H), 3.91 (t, 2H), 3.16 (t, 2H), 2.58 (s, 3H), 1.80 (m, 4H), 1.14-1.05 (m/m, 4H), 0.88 (s, 9H), 0.85 (t, 6H), 0.00 (s, 6H).

MS (m/z): 423 [MH]$^+$.

Intermediate 15

(2,4-Bis-trifluoromethyl-phenyl)-[3-[2-(tert-Butyl-dimethyl-silanyloxy)-ethyl]-6-methyl-(1-propyl-butyl)-1-1H-pyrrolo[3,2-c]pyridin-4-yl]-amine To a mixture of tris(dibenzylideneacetone)palladium(0) (3.7 mg, 0.1 eq), 2-(dicyclohexylphosphino)-2'-methylbiphenyl (4.4 mg, 0.3 eq), K$_3$PO$_4$ (23 mg, 2.8 eq) a solution of intermediate 14 (17 mg, 0.04 mmol) and 2,4-bis(trifluoromethyl)anilin (18 mg, 2 eq) in anh. DME (1 mL) at r.t., under $N_2$, was added (crimp cap microwave vial). The reaction mixture was irradiated in CEM Focused Microwave Synthesis System (Model Discovery), at 100° C., 150 W, 60 Psi for 20 min (cooling on). Then water (1 mL) was added and the product was extracted with Et$_2$O (3×5 mL). The combined organic layers were washed with sat.aq. NaCl (1×5 mL) and dried over anh. $Na_2SO_4$. The solids were filtered and the solvent evaporated to give a crude product, which was purified by flash chromatography (silica gel, cHex/EtOAc 95:05). The desired product was obtained as a yellow oil (21.5 mg, 0.035 mmol, 88%).

NMR ($^1$H, DMSO): δ 7.83 (d, 1H), 7.79 (dd, 1H), 8.16 (d, 1H), 8.23 (s, 1), 7.22 (s, 1H), 7.16 (s, 1H), 2.43 (s, 3H), 4.35 (m, 1H), 3.77 (t, 2H), 2.94 (t, 2H), 1.8 (m, 4H), 1.15, 0.95 (m/m, 4H), 0.79 (t, 6H), 0.68 (s, 9H), −0.31 (s, 6H). MS (m/z): 616 [MH]$^+$.

Intermediate 16

2-[4-(2,4-Bis-trifluoromethyl-phenyl)-6-methyl-1-(1-propyl-butyl)-1H-pyrrolo[3,2-c]pyridin-3-yl]-ethanol To a solution of intermediate 15 (60 mg, 0.097 mmol) in dry DMF (5 mL) at r.t. Et$_3$N.3HF (133.6 μL, 8.4 eq) was added. The reaction mixture was stirred at r.t. overnight. Then water (2 mL) was added and the product was extracted with EtOAc (3×5 mL). The combined organic layers were washed with sat.aq. NaCl (1×5 mL) and dried over anh. $Na_2SO_4$. The solids were filtered and the solvent evaporated to give a crude product, which was purified by flash chromatography (silica gel, cHex/EtOAc 9:1). The desired product was obtained as a white solid (24.4 mg, 0.048 mmol, 50%).

NMR ($^1$H, DMSO): δ 9.01 (sa, 1H), 8.07 (d, 1H), 7.81 (s, 1H), 7.76 (dd, 1H), 7.19 (s, 1H), 7.10 (s, 1H), 5.19 (sa, 1H), 4.35 (m, 1H), 3.63 (m, 2H), 2.88 (m, 2H), 2.38 (s, 3H), 1.85-1.65 (m, 4H), 1.20, 0.90 (m, 4H), 0.80 (m, 6H). MS (m/z): 502 [MH]$^+$.

Intermediate 17

5-(2,4-Bis-trifluoromethyl-phenyl)-7-methyl-1-(1-propyl-butyl)-1,3,4,5-tetrahydro-1,5,6-triaza-acenaphthylene To a solution of intermediate 16 (23.4 mg, 0.04 mmol) in dry CH$_2$Cl$_2$ (2 mL) at r.t. Et$_3$N (13.5 L, 2 eq) and MsCl (6.16 μL, 2 eq) were added. The reaction mixture was stirred at r.t. for 2 hr. Then water (2 mL) was added and the product was extracted with CH$_2$Cl$_2$ (3×5 mL). The combined organic layers were washed with sat.aq. NaCl (1×5 mL) and dried over anh. $Na_2SO_4$. The solids were filtered and the solvent evaporated to give a crude product, which was purified by flash chromatography (silica gel, cHex/EtOAc 9:1). The desired product was obtained as a yellow oil (6 mg, 0.012 mmol, 31%).

NMR ($^1$H, DMSO): δ 8.08 (dd, 1H), 8.03 (s, 1H), 7.81 (d, 1H), 6.87 (s, 1H), 6.61 (s, 1H), 4.19 (m, 1H), 3.72 (t, 2H), 3.02 (t, 2H), 2.19 (s, 3H), 1.80-1.70 (m, 4H1), 1.30-1.10 (m, 4H), 0.79 (m, 6H). MS (m/z): 483 [MH]+.

EXAMPLE 1

Synthesis of Representative Compounds of Structure (IVb)

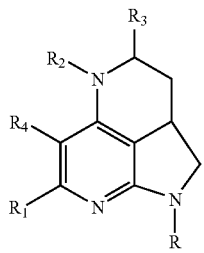

(IVb)

Compound 1-1

1-(4-Methoxy-2-methylphenyl)-7-methyl-5-(1-propyl-butyl)-1,2,2a,3,4,5-hexahydro-1,5,8-triaza-acenaphtylene 4-methoxy-2-methyl aniline (19 µL, 1.3 eq) and sodium triacetoxyborohydride (36 mg, 1.5 eq) were added to intermediate 8 (30 mg, 1.0 eq) in 1 mL CH$_2$Cl$_2$. The reaction was stirred at room temp for two hours. Then the solvent was removed, phenyl ether (1 mL), and PTSA (22 mg, 1.0 eq) were added. The reaction was heated to 225° C. for 45 min. The reaction was diluted with hexanes (10 mL) and the product extracted with 1N HCl (3×10 mL). The aqueous extracted were washed with ether (3×25 mL), neutralized with NaHCO$_3$, extracted with ethyl acetate (3×50 mL), washed with brine, dried over sodium sulfate, filtered and concentrated in vacuo. The residue was purified by preparative TLC to yield the desired product (5 mg, 13% two steps), R$_f$=0.15 in 60% ethyl acetate/hexanes

Compound 1-2

1-(2,4-Dimethylphenyl)-7-methyl-5-(1-propyl-butyl)-1,2,2a,3,4,5-hexahydro-1,5,8-triaza-acenaphtylene The same methodology used to make compound 1-1 was used to make the desired product except the aniline used was 2,4-dimethylaniline (18 mg, 0.15 mmol). The residue was purified by preparative TLC to yield 4 mg (9% two steps) of the desired product, R$_f$=4.37 in 60% ethyl acetate/hexanes.

Compound 1-3

1-(2-Chloro-4-methylphenyl)-7-methyl-5-(1-propyl-butyl)-1,2,2a,3,4,5-hexahydro-1,5,8-triaza-acenaphtylene The same methodology used to make compound 1-1 was used to make the desired product except the aniline used was 2-chloro-4-methylaniline (21 mg, 0.15 mmol). The residue was purified by preparative TLC to yield 9.2 mg (20% two steps) of the desired product, R$_f$=0.52 in 60% ethyl acetate/hexanes.

All the analytical data are set forth in the following Table 1.

TABLE 1

(IVb)

| Cpd. No. | R | R$_1$ | R$_2$— | R$_3$—R$_4$— | Analytical Data |
|---|---|---|---|---|---|
| 1-1 | 2-methyl-4-methoxyphenyl | CH$_3$ | (1-propyl-butyl) | H | MS (M + 1) 394. $^1$H NMR (CDCl$_3$) δ: 7.15 (d, 1H), 6.85 (d, 1H), 6.8 (dd, 1H) 6.93 (s, 1H), 4.02 (t, 1H), 3.8 (s, 3H), 3.7 (m, 2H), 3.5 (m, 3H), 3.15 (dt, 2H), 2.45 (s, 3H), 2.33 (s, 3H), 1.6 (m, 4H), 1.26 (m, 4H), 0.95 (t, 6H). |
| 1-2 | 2,4-dimethylphenyl | CH$_3$ | (1-propyl-butyl) | H | MS (M + 1) 378. $^1$H NMR (CDCl$_3$) δ: 7.16 (d, 1H), 7.08 (m, 2H), 5.92 (s, 1H), 4.02 (t, 2H), 3.74 (m, 3H), 3.42 (m, 2H), 3.12 (m, 1H), 2.48 (s, 3H), 2.32 (s, 3H), 1.58 (m, 4H), 1.28 (m, 4H), 0.94 (t, 6H). |

TABLE 1-continued (IVb)

| Cpd. No. | R | $R_1$ | $R_2$— | $R_3$—<br>$R_4$— | Analytical Data |
|---|---|---|---|---|---|
| 1-3 | 2-chloro-4-methylphenyl | $CH_3$ | (propyl-butyl group) | H | MS (M + 1) 398.<br>$^1$H NMR (CDCl$_3$) δ: 7.35 (d, 1H), 7.25 (d, 1H), 7.10 (dd, 1H), 5.96 (s, 1H), 4.1 (t, 2H), 3.76 (m, 1H), 3.6 (m, 2H), 3.4 (m, 2H), 3.06 (m, 1H), 2.38 (s, 3H), 2.3 (s, 3H), 1.56 (m, 4H), 1.26 (m, 4H), 0.92 (t, 6H). |

EXAMPLE 2

Synthesis of Representative Compounds of Structure (IVa)

(IVa)

Compound 2-1

9-(2,4-Dimethyl-phenyl)-2-methyl-4-(1-propyl-butyl)-5,6,6a,7,8,9-hexahydro-4H-1,4,9-triaza-phenalene The same methodology used to make compound 1-1 from intermediate 8 was used to make the desired product from intermediate 10. The organic residue was purified by preparative TLC to yield (11 mg, 10% two steps).
$R_f$=0.14 in 100% ethyl acetate.

Compound 2-2

9-(4-Methoxy-2-methyl-phenyl)-2-methyl-4-(1-propyl-butyl)-5,6,6a,7,8,9-hexahydro-4H-1,4,9-triaza-phenalene The same methodology used to make compound 2-1 was used to make the desired product except the aniline used was 4-methoxy-2-methylaniline. The organic residue was purified by preparative TLC to yield (63 mg, 56% two steps).
$R_f$=0.0 in 100% ethyl acetate.

All the analytical data are set forth in the following Table 2.

TABLE 2

| Cpd. No. | R | $R_1$ | $R_2$— | $R_3$—<br>$R_4$— | Analytical Data |
|---|---|---|---|---|---|
| 2-1 | 2,4-dimethyl-phenyl | $CH_3$ | (propyl-butyl group) | H | MS (M + 1) 392.<br>$^1$H NMR (CDCl$_3$) δ: 7.08 (m, 3H), 5.9 (s, 1H), 3.84 (m, 1H), 3.62 (m, 2H), 3.3 (dq, 1H), 3.08 (dt, 2H), 2.79 (m, 1H), 2.36 (s, 3H), 2.12 (s, 6H), 2.45 (m, 4H), 1.26 (m, 4H), 0.9 (t, 6H). |
| 2-2 | 2-methyl-4-methoxy | $CH_3$ | (propyl-butyl group) | H | MS (M + 1) 408<br>$^1$H NMR (CDCl$_3$) δ: 7.1 (d, 1H), 6.75 (m, 2H), 5.85 (s, 1H), 3.8 (s, 3H), 3.64 (m, 2H), 3.36 (m, 2H), 3.24 (dt, 2H), 3.04 (dt, 1H), 2.1 (s, 6H), 1.75 (m, 2H), 1.4 (m, 8H), 0.9 (bs, 6H). |

EXAMPLE 3

Synthesis of Representative Compounds of Structure (IVc)

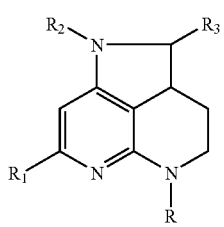

Compound 3-1

5-(2,4-Bis-trifluoromethyl-phenyl)-7-methyl-1-(1-propyl-butyl)-1,2,2a,3,4,5-hexahydro-1,5,6-triaza-acenaphtylene Intermediate 17 is subjected to reduction with a suitable reducing agent for enamine derivatives, such as Mg/MeOH or $NaBH_4$.

EXAMPLE 4

CRF Binding Activity

CRF binding affinity has been determined in vitro by the compounds' ability to displace $^{125}$I-oCRF and $^{125}$I-Sauvagine for CRF1 and CRF2 SPA, respectively, from recombinant human CRF receptors expressed in Chinese Hamster Ovary (CHO) cell membranes. For membrane preparation, CHO cells from confluent T-flasks were collected in SPA buffer (HEPES/KOH 50 mM, EDTA 2 mM; $MgCl_2$ 10 mM, pH 7.4.) in 50 mL centrifuge tubes, homogenized with a Polytron and centrifuged (50,000 g for 5 min at 4° C.: Beckman centrifuge with JA20 rotor). The pellet was resuspended, homogenized and centrifuged as before.

The SPA experiment has been carried out in Optiplate by the addition of 100 µL the reagent mixture to 1 L of compound dilution (100% DMSO solution) per well. The assay mixture was prepared by mixing SPA buffer, WGA SPA beads (2.5 mg/mL), BSA (1 mg/mL) and membranes (50 and 5 µg of protein/mL for CRF1 and CRF2 respectively) and 50 pM of radioligand.

The plate was incubated overnight (>18 hr) at room temperature and read with the Packard Topcount with a WGA-SPA $^{125}$I counting protocol.

EXAMPLE 5

CRF Functional Assay

Compounds of the invention were characterised in a functional assay for the determination of their inhibitory effect. Human CRF-CHO cells were stimulated with CRF and the receptor activation was evaluated by measuring the accumulation of cAMP.

CHO cells from a confluent T-flask were resuspended with culture medium without G418 and dispensed in a 96-well plate, 25,000 c/well, 100 µL/well and incubated overnight. After the incubation the medium was replaced with 100 µL of cAMP IBMX buffer warmed at 37° C. (5 mM KCl, 5 mM $NaHCO_3$, 154 mM NaCl, 5 mM HEPES, 2.3 mM $CaCl_2$, 1 mM $MgCl_2$; 1 g/L glucose, pH 7.4 additioned by 1 mg/mL BSA and 1 mM IBMX) and 1 µL of antagonist dilution in neat DMSO. After 10 additional minutes of incubation at 37° C. in a plate incubator without $CO_2$, 1 µL of agonist dilution in neat DMSO was added. As before, the plate was incubated for 10 minutes and then cAMP cellular content was measured by using the Amersham RPA 538 kit.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound according to formula (I), and stereoisomers, prodrugs and pharmaceutically acceptable salts or solvates thereof

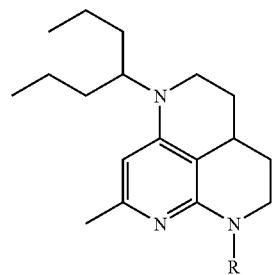

wherein

R is phenyl which may be substituted by 1 to 4 substituents independently selected from the group consisting of:

halogen, C1-C6 alkyl, C1-C6 alkoxy, halo C1-C6 alkyl, C2-C6 alkenyl, C2-C6 alkynyl, halo C1-C6 alkoxy, C1-C6 mono or dialkylamino, nitro, cyano and a group $R_5$; and $R_5$ is C3-C7 cycloalkyl, which may contain one or more double bonds; aryl; or a 5-6 membered heterocycle; wherein each of the above groups $R_5$ may be substituted by one or more groups selected from: halogen, C1-C6 alkyl, C1-C6 alkoxy, halo C1-C6 alkyl, C2-C6 alkenyl, C2-C6 alkynyl, halo C1-C6 alkoxy, C1-C6 mono or dialkylamino, nitro, and cyano.

2. A compound, according to claim 1, wherein

R is selected from: 2,4-dichloro phenyl, 2-chloro-4-methylphenyl, 2-chloro-4-trifluoromethylphenyl, 2-chloro-4-methoxyphenyl, 2,4,5-trimethyiphenyl, 2,4-dimethyl-phenyl, 2-methyl-4-methoxyphenyl, 2-methyl-4-chlorophenyl, 2-methyl-4-trifluoromethyiphenyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropyiphenyl, 2-methoxy-4-methylphenyl, 2-trifluoromethyl-4-chlorophenyl, 2,4-trifluoromethyiphenyl, 2-trifluoromethyl-4-methylphenyl, 2-trifluoromethyl-4-methoxy-phenyl, 2-bromo-4-isopropylphenyl, 2-methyl-4-cyanophenyl, 2-chloro-4-cyanophenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl.

3. A compound, according to claim 1, selected from the group consisting of:

9-(2,4-dimethyl-phenyl)-2-methyl-4-(1-propyl-butyl)-5,6,6a,7,8,9-hexahydro-4H-1,4,9-triaza-phenalene; and 9-(4-methoxy-2-methyl-phenyl)-2-methyl-4-(1-propyl-butyl)-5,6,6a,7,8,9-hexahydro-4H-1,4,9-triaza-phenalene.

4. A pharmaceutical composition comprising a compound according to claim 1 in admixture with one or more physiologically acceptable carriers or excipients.

5. A method for the treatment of, comprising administration of an effective amount of a compound according to claim 1, to a mammal in need of treatment thereof.

6. A method for the treatment of anxiety, comprising administration of an effective amount of a compound according to claim 1, to a mammal in need of treatment thereof.

* * * * *